United States Patent [19]

Sørensen

[11] Patent Number: 5,547,696
[45] Date of Patent: Aug. 20, 1996

[54] PHARMACEUTICAL FORMULATION

[75] Inventor: Hans H. Sørensen, Virum, Denmark

[73] Assignee: Novo Nordisk A/S, Bagsvaerd, Denmark

[21] Appl. No.: 322,260

[22] Filed: Oct. 13, 1994

[51] Int. Cl.$^6$ .............................. A61K 9/14; A61K 9/08; A61K 38/27
[52] U.S. Cl. ............................ 424/499; 424/490; 514/21; 514/2
[58] Field of Search .................................. 424/499, 490; 514/21, 2

[56] References Cited

U.S. PATENT DOCUMENTS

| | | | |
|---|---|---|---|
| 4,537,769 | 8/1985 | Cerini | 424/89 |
| 4,915,945 | 4/1990 | Pelzer | 421/101 |
| 4,917,685 | 4/1990 | Viswanathan | 604/891 |
| 5,041,378 | 8/1991 | Drummond | 435/234 |

FOREIGN PATENT DOCUMENTS

| | | |
|---|---|---|
| 0106608 | 4/1984 | European Pat. Off. . |
| 0303746 | 2/1989 | European Pat. Off. . |
| 0374120 | 6/1990 | European Pat. Off. . |
| 89/09614 | 10/1989 | WIPO . |
| 93/12812 | 7/1993 | WIPO . |
| 93/12811 | 7/1993 | WIPO . |
| 93/19776 | 10/1993 | WIPO . |
| 94/03198 | 2/1994 | WIPO . |

OTHER PUBLICATIONS

Wang et al., J. Parenteral Sci. & Tech., Vo. 42, pp. s3–s26 (1988).
Manning et al., Pharma. Research, vol. 6. No. 11, pp. 903–918 (1989).
Becker et al., Biotech. and Applied Biochem., vol. 9, 478–487 (1987).
Johnson et al., J. Biol. Chem., vol. 264, No. 24, pp. 14262–14271 (1989).
Becker et al., Biotech. and Applied Biochem., vol. 10, 326–337 (1988).
Houghten et al., Ach. Biochem. & Biophy., vol. 178, pp. 350–355 (1977).
Teh et al., J. Biological Chem., vol. 262, No. 14, pp. 6472–6477 (1987).
Riggin et al., Analytical Biochem., vol. 167, pp. 199–209 (1987).
Gellerfors, Acta Pædiatr Scand [Suppl], vol. 370, pp. 93–100 (1990).
Kaufman, Pharmaceutical Research, vol. 7, No. 3, pp. 289–293 (1990).
Dialog accession No. 004842401, WPI accession No. 86–345742/52.
Dialog accession No. 007545021, WPI accession No. 88–178953/26.

*Primary Examiner*—Gollamudi S. Kishore
*Attorney, Agent, or Firm*—Steve T. Zelson, Esq.; Cheryl H. Agris, Esq.

[57] ABSTRACT

A pharmaceutical formulation comprising a growth hormone and valine as additive or buffering substance shows a very high stability against deamidation, oxidation and cleavage of peptide bonds. The stability of the product allows for the storing and shipment thereof in a lyophilized state or in the form of a dissolved or re-dissolved formulation at ambient temperature.

12 Claims, No Drawings

PHARMACEUTICAL FORMULATION

FIELD OF THE INVENTION

The present invention relates to a stabilized pharmaceutical formulation comprising growth hormone, to a method of making such formulation, and the use of valine for stabilizing a formulation of growth hormone.

BACKGROUND OF THE INVENTION

The growth hormones from man and from the common domestic animals are proteins of approximately 191 amino acids, synthesized and secreted from the anterior lope of the pituitary gland. Human growth hormone consists of 191 amino acids.

Growth hormone is a key hormone involved in the regulation of not only somatic growth, but also in the regulation of metabolism of proteins, carbohydrates and lipids. The major effect of growth hormone is to promote growth.

The organ systems affected by growth hormone include the skeleton, connective tissue, muscles, and viscera such as liver, intestine, and kidneys.

Until the development of the recombinant technology and the cloning of the growth hormone gene now giving rise to production of e.g. human growth hormone (hGH) and Met-hGH in industrial scale, human growth hormone could only be obtained by extraction from the pituitary glands of human cadavers. The very limited supplies of growth hormone restricted the use thereof to longitudinal growth promotion in childhood and puberty for treatment of dwarfism, even though it has been proposed for inter alia treatment of short stature (due to growth hormone deficiency, normal short stature and Turner syndrome), growth hormone deficiency in adults, infertility, treatment of burns, wound healing, dystrophy, bone knitting, osteoporosis, diffuse gastric bleeding, and pseudoarthrosis.

Furthermore, growth hormone has been proposed for increasing the rate of growth of domestic animals or for decreasing the proportion of fat in animals to be slaughtered for human consumption.

Pharmaceutical formulations of growth hormone tend to be unstable. Degradation products such as deamidated or sulfoxydated products and dimer or polymer forms are generated—especially in solutions of growth hormone.

The predominant degradation reactions of hGH are 1) deamidation by direct hydrolysis or via a cyclic succinimide intermediate to form various amounts of L-asp-hGH, L-iso-asp-hGH, D-asp-hGH, and D-iso-asp-hGH (ref 1–3), and 2) oxidation of the methionine residues in positions 14 and 125 (ref 4–9). The major degradation product of hGH in lyophilized state as well as in solution is deamidated hGH.

Deamidation especially takes place at the Asn in position 149 and to a minor extent in position 152.

hGH is rather easily oxidized in positions 14 and 125, especially in solution (4–8).

The oxidation of hGH in solution forming sulfoxides is normally due to the oxygen dissolved in the formulation. The solubility of oxygen in distilled water is about 200 $\mu$M (9). As the concentration of hGH in a formulation comprising 4 IU/ml is 1.3 mg/ml corresponding to 60 nM hGH, oxygen will, at normal storing conditions, be present in an excess of about 3000 times the stoichiometric amount for oxidation of hGH. It is not feasible to try to solve the problem by degassing of buffers before tapping and packing the formulations.

At present, it is not believed that these deamidated forms and oxidized forms should have toxic or altered biological activity or receptor binding properties, but there is indication to the effect that the conformation stability of the sulfoxides is reduced as compared to native hGH.

For the development of a stable, dissolved formulation comprising hGH it is of importance to know the rate of deamidation and formation of sulfoxides as well as means to control the reactions.

The kinetics of degradation depend on temperature, pH and various additives or adjuvants in the hGH formulation.

Due to the instability, growth hormone is, at present, lyophilized and stored in the lyophilized form at 4° C. until it is reconstituted for use in order to minimize the degradation.

The lyophilized pharmaceutical formulations comprising hGH are, at present, reconstituted by the patient and then stored as a solution during the use for a period of up to 14 days at 4° C., during which some degradation will take place.

Furthermore, the process of reconstitution of the lyophilized growth hormone tends to provide difficulties for the patient.

Thus, it is at present preferred to reconstitute the growth hormone as late as possible before use and to store and ship the formulation in a lyophilized state. The chain from the manufacturer to the pharmacy is apt for handling the formulations at a controlled low temperature of e.g. 4° C. which allows for a long shelf life of up to two years.

However, the extended use of pen systems for self-medication and the expanded field of use calls for a formulation which is stable for a sufficient long time with the end user under conditions where "sufficient" cooling is not always available.

Preferably, a formulation should be stable with the end user in a lyophilized state for about one month and additionally for one month in a reconstituted state in a pen device for the intended period of use of a cartridge.

Thus, there is a need for more stable formulations of growth hormone being stable in a lyophilized state at a relative high temperature for a period and additionally for a period of use at a relatively high temperature in solution. Such stabilization is of very great importance when moving the administration of the growth hormone from clinics to the homes of the individuals to be treated where optimal storage may not be available as indicated above.

Furthermore, the shift in pattern of administration of growth hormone to the use of pen devices calls for a stable dissolved formulation comprising growth hormone in order to facilitate the handling to be performed by the patient. A stable dissolved formulation comprising growth hormone may be produced ready to use in the form of cartridges fitting into the pen device used by the patient who may then avoid the reconstitution of the formulation and, hence, will not have to be in the possession of a lyophilized formulation, a suitable vehicle for reconstitution as well as the necessary skill and sterile equipment for sterile reconstitution of the formulation.

For safety reasons it will also be deskable to avoid the reconstitution of a lyophilized formulation just before the use of the formulation.

Furthermore, it would also be an advantage to avoid the lyophilization step in the production of growth hormone formulations. Lyophilization is a time consuming and cosily process and is also often a "bottleneck" in the production due to the limited capacity of the freeze drier.

Thus, there is a need to reduce the rate of the degradation processes in order to allow for dissolved hGH formulations being stable during shelf life and during the period of use of up to one month.

Prior attempts to stabilize hGH has not fully succeeded in preventing the formation of dimer. The problems associated with dimer formation is e.g. noted in Becker, *Biotechnology and Applied Biochemistry* 9, 478 (1987).

International Patent Publication No. WO 89/09614 and Australian patent application No. 30771/89 disclose a stable pharmaceutical formulation containing human growth hormone, glycine, and mannitol. Such a formulation shows improved stability during normal processing and storage in a lyophilized state as well as in the period of use after the reconstitution.

Published European patent application No. 303 746 discloses that animal growth hormone may be stabilized with various stabilizers to give decreased formation of insolubles and preservation of the soluble activity in aqueous environments, such stabilizers including certain polyols, amino acids, polymers of amino acids having a charged side group at physiological pH, and choline salts. Polyols are selected from the group consisting of non-reducing sugars, sugar alcohols, sugar acids, pentaerythritol, lactose, water-soluble dextrans and Ficoll; amino acids are selected from the group consisting of glycine, sarcosine, lysine or salts thereof, serine, arginine or salts thereof, betaine, N,N,-dimethylglycine, aspartic acid or salts thereof, glutamic acid or salts thereof; a polymer of an amino acid having a charged side group at physiological pH may be selected from polylysine, polyaspartic acid, polyglutamic acid, polyarginine, polyhistidine, polyornithine and salts thereof; and choline derivatives are selected from the group consisting of choline chloride, choline dihydrogen citrate, choline bitartrate, choline bicarbonate, tricholine citrate, choline ascorbate, choline borate, choline gluconate, choline phosphate, di(choline)sulphate and dicholine mucate.

U.S. Pat. No. 4,917,685 discloses a delivery device designed to be implanted comprising growth hormone stabilized using the same stabilizers as mentioned in EP 303746.

Published European patent application No. 374,120 discloses a stabilized formulation comprising hGH and a polyol having three hydroxy groups. Glycerol and tris(hydroxyEmethyl)aminomethane are mentioned. Furthermore, the presence of histidine hydrochloride as a buffer together with the polyol is disclosed.

International Patent Publication No. WO 93/12811 discloses stabilized formulations of growth hormone in the form of a lyophilized powder or an aqueous solution comprising asparagine.

International Patent Publication No. WO 93/12812 discloses stabilized formulations of growth hormone in the form of a lyophilized powder or an aqueous solution comprising histidine.

International Patent Publication No. WO 93/19776 discloses protein formulations comprising growth hormone comprising citrate as buffer substance being more stable than formulations comprising phosphate buffer. The formulations may also comprise amino acids such as glycine and alanine and/or mannitol or other sugar alcohols and/or glycerol and/or other carbohydrates and optionally a preservative such as benzyl alcohol.

International Patent Publication No. WO 94/03198 discloses a stable aqueous formulation containing human growth hormone, a buffer, a non-ionic surfactant, and, optionally, a neutral salt, mannitol, or, a preservative.

BRIEF DESCRIPTION OF THE INVENTION

It has now surprisingly been found that a formulation of human growth hormone comprising valine as additive shows a very high stability against deamidation and oxidation. The stability of the product allows for the storing and shipment thereof in a lyophilized state or in the form of a dissolved or re-dissolved formulation.

The pharmaceutical formulations of the invention may be formulated for administration in any suitable way, e.g. by parenteral or oral administration or administration to a mucosal membrane, e.g. nasal, buccal, sublingual, or vaginal administration. The pharmaceutical formulation may be presented in the form of a dose comprised in a vial or cartridge or any other suitable container such as a prefilled syringe or a pen device.

Thus, the formulation of the invention may be in the form of a lyophilized powder to be reconstituted later using conventional vehicles such as distilled water or water for injection or in the form of a solution comprising growth hormone. Such vehicles may comprise conventional preservatives such as m-cresol and benzyl alcohol.

A preferred embodiment of the invention is in the form of a pharmaceutical formulation of human growth hormone comprising valine and further comprising a carrier in the form of a buffered aqueous solution of growth hormone. Such formulation is in a ready-to-use form and may be stored and shipped as an aqueous solution without any considerable degradation.

A buffer to be used in a solution of growth hormone may e.g. be histidine, citrate, tartrate or phosphate buffer.

For stability reasons the pH of a solution is preferably adjusted to a value in the interval from about 2 to about 8, more preferred to pH from 5 to 7, especially to pH about 6.8.

In order to obtain the stabilizing effect valine is preferably added in an amount of up to 100 mM, more preferred in an amount of about 5 mM.

The pharmaceutical formulation of the invention may furthermore comprise salts for adjusting the tonicity and optionally an excipient in order to facilitate the processing thereof, e.g. lyophilization and the rapid and complete dissolution of a lyophilized formulation when reconstituting the formulation before use.

An excipient may be selected from disaccharides such as lactose, trehalose, and sucrose, sugar alcohols such as sorbitol or mannitol, polysaccharides such as the polymers commercialized as Dextran® products such as Dextran® 40, Dextran®70 or Dextran® 75, and Ficoll® and polyvalent alcohols such as polyethylene glycol or polyvinyl alcohol or a combination of two or more of these.

In a further aspect the invention relates to a method of preparing a pharmaceutical formulation comprising a growth hormone and valine wherein the growth hormone is dissolved in a solution comprising valine by dissolving valine in deionized water optionally containing of benzyl alcohol, adding the growth hormone and optionally adjusting the pH to from about 2 to about 8.

The pH may be adjusted by adding an acid which has no adverse effect on the growth hormone, preferably a physiologically acceptable acid e.g. a mineral acid such as hydrochloric acid, sulphuric acid or nitric acid or an organic acid such as acetic acid.

In an embodiment of the method of the invention, is added optionally salts and an excipient, whereafter the solution is filled into a container and lyophilized.

Still another aspect of the invention relates to the use of valine for the formulation of a stabilized formulation of growth hormone.

In the present context "growth hormone" may be growth hormone from any origin such as avian, bovine, equine, human, ovine, porcine, salmon, trout or tuna growth hormone, preferably bovine, human or porcine growth hormone, human growth hormone being most preferred. The growth hormone used in accordance with the invention may be native growth hormone isolated from a natural source, e.g. by extracting pituitary glands in a conventional manner, or a growth hormone produced by recombinant techniques, e.g. as described in Jensen et al., Biotech and Bioeng. 36, 1–11 (1990). The "growth hormone" may also be a truncated form of growth hormone wherein one or more amino acid residues has (have) been deleted; an analogue thereof wherein one or more amino acid residues in the native molecule has (have) been substituted by another amino acid residue, preferably a natural amino acid residue, as long as the substitution does not have any adverse effect such as antigenicity or reduced action; or a derivative thereof, e.g. having an N- or C-terminal extension such as Met-hGH. The preferred growth hormone is hGH.

The term "dose" of growth hormone refers to that amount that provides therapeutic effect in an administration regimen. The formulations hereof are prepared containing amounts of hGH at least about 0.1 mg/ml, preferably upwards of about 10 mg/ml, preferably from about 1 mg/ml to about 40 mg/ml, more preferably from about 1 mg/ml to about 25 mg/ml, e.g. from 1 mg/ml to about 5 mg/ml, calculated on the ready-to-use formulation. For use of these compositions in administration to human beings suffering from hypopituitary dwarfism, for example, these formulations contain from about 0.1 mg/mg to about 10 mg/ml, corresponding to the currently contemplated dosage regimen for the intended treatment. The concentration range is not critical to the invention and may be varied by the physician supervising the administration.

Valine to be used in accordance with the present invention is preferably naturally occurring alpha valine. The valine may be l or d valine or a mixture thereof.

In the present context "high stability" is obtained when the formulation is more stable than the conventional formulation comprising phosphate buffer.

The solvent used in the method of the invention may be water, alcohols such as ethyl, n-propyl or isopropyl, butyl alcohol or mixtures thereof. The solvent may comprise a preservative such as m-cresol or benzyl alcohol.

DETAILED DESCRIPTION OF THE INVENTION

The invention is explained more in detail in the below Examples which illustrate the invention. They are not to be considered as limiting the scope of the invention being defined by the appended claims.

EXPERIMENTAL PART

EXAMPLE

Reduction of the deamidation.

The rate of deamidation was examined at 4° C. and 25° C. for hGH formulations comprising 2 mg hGH at pH 6.8 in the presence of 5 mM Val as compared to 8 mM phosphate buffer at pH 6.8 and various other amino acids at pH 6.8.

The hGH formulations were prepared by dissolving 4 mg hGH in 2 ml of 10 mM solution of amino acid. Then, 2 ml 1.8% of benzyl alcohol was added to give a final formulation of 2 mg/ml hGH, 5 mM amino acid, 0.9% benzyl alcohol pH 6.8 (adjusted by adding HCl or NaOH).

The hGH formulations stated in the below table were stored at 25° C. for 32 days, and at 4° C. for 2 years and analyzed for the contents of deamidated hGH by IE-HPLC. The results appear from the below table.

TABLE

| Formulation* | Content of deamidated hGH | |
|---|---|---|
| | 24 months at 4° C. | 32 days at 25° C. |
| L—Ala | 35.7 | 19.3 |
| Alaninol | 23.5 | 17.7 |
| L—Arg | 26.0 | 17.2 |
| L—Met | 26.5 | 18.7 |
| L—Cys | 41.1 | 24.1 |
| L—Pro | 25.4 | 18.3 |
| L—Ser | 32.8 | 21.4 |
| L—Thr | 29.5 | 20.1 |
| L—Trp | 27.4 | 19.5 |
| L—Lys | 33.0 | 21.0 |
| L—Val | 20.7 | 15.6 |
| 8 mM $Na_2HPO_4$, $2H_2O$ | 30.1 | 23.3 |
| 1 mM His | 23.7 | 15.1 |

The contents of deamidated hGH in the starting material was: 2.0%

From the above table it appears that the deamidation of hGH is reduced by approximately 30% by addition of valine as compared with phosphate buffer. Furthermore, a stabilization of hGH by addition of valine of the same order with respect to deamidation as compared to Ala, Alaninol, Arg, Met, Cys, Pro, Ser, Thr, Trp, and Lys was observed.

The above results show that the rate of deamidation is reduced by adding valine in a low concentration of up to 100 mM, preferably about 5 mM. The rate of deamidation may be reduced by more than 30 by substituting the phosphate buffer with valine.

The use of benzyl alcohol as preservative seems to have no influence on the rate of deamidation.

REFERENCES

1) Wang et al., Parenteral Formulations of Proteins and Peptides: Stability and Stabilizers. J. Parenteral Science and Technology 42 (Suppl.) (1988) 53–525.
2) Manning et al., Stability of Protein Pharmaceuticals. Pharmaceutical Research 6 (11) (1989) 903–918.
3) Johnson et al., J. Biol. Chem. 264, 1462–71 (1989).
4) Teh et al., J. Biol. Chem., 262, 785–794 (1987).
5) Becker et al., Biotech. Appl. Biochem., 10, 326–337 (1988).
6) Houghten et al., Arch. Biochem. Biophys., 178, 350–355 (1977).
7) Riggin et al., Anal. Biochem., 167, 199–209 (1987).
8) Gellerfors et al., Acta Paediatr. Scand (suppl), 370, 93–100 (1990).
9) Kaufman, Pharm. Res., 7 (3) 289–292 (1990).

I claim:
1. A pharmaceutical formulation comprising a growth hormone in the amount of about 0.1 mg/ml to about 40 mg/ml and valine at a concentration up to about 100 mM.

2. The pharmaceutical formulation according to claim 1 wherein the formulation is in the form of a buffered aqueous solution.

3. The pharmaceutical formulation according to claim 1, wherein the pH is in the range of about 2 to about 8.

4. The pharmaceutical formulation according to claim 1, wherein the formulation further comprises saccharides.

5. The pharmaceutical formulation according to claim 1, wherein the growth hormone is hGH.

6. A method of preparing the pharmaceutical formulation according to claim 1, comprising dissolving the growth hormone in a solution comprising valine.

7. The method according to claim 6 in which the solution comprising valine is obtained by dissolving valine in deionized water.

8. The method according to claim 6 in which the solution comprising valine is obtained by dissolving valine in deionized water containing benzyl alcohol.

9. The method according to claim 6 in which the pH is adjusted to from about 2 to about 8.

10. The method according to claim 6 which further comprises adding an excipient to said solution and lyophilizing said solution.

11. A method of stabilizing a formulation of growth hormone in the amount of about 0.1 mg/ml to about 40 mg/ml, comprising adding valine to the formulation in an amount effective to stabilize said formulation.

12. A method of treating a disorder in a patient affectable by growth hormone comprising treating the patient with an amount of the pharmaceutical formulation of claim 1 effective to treat said disorder.

* * * * *